United States Patent [19]

Kline

[11] Patent Number: 5,749,838

[45] Date of Patent: May 12, 1998

[54] POSTURE TRAINING DEVICE

[76] Inventor: Daniel S. Kline, P.O. Box 188236, Carlsbad, Calif. 92009

[21] Appl. No.: 578,559

[22] PCT Filed: Dec. 1, 1995

[86] PCT No.: PCT/US95/15631

§ 371 Date: Dec. 29, 1995

§ 102(e) Date: Dec. 29, 1995

[87] PCT Pub. No.: WO96/17548

PCT Pub. Date: Jun. 13, 1996

[51] Int. Cl.$^6$ ........................................... A61H 11/00
[52] U.S. Cl. .................... 601/71; 128/781; 340/573
[58] Field of Search .................... 601/71; 128/721, 128/781, 782, 845, 870; 340/573, 666, 689; 482/148, 909; 116/67 R; 602/19

[56] References Cited

U.S. PATENT DOCUMENTS

| | | | |
|---|---|---|---|
| 2,263,670 | 11/1941 | Arkin | 119/108 |
| 3,582,935 | 6/1971 | Verhaeghe | 340/279 |
| 3,608,541 | 9/1971 | Hall | 128/2 |
| 3,644,919 | 2/1972 | Mathauser | 340/279 |
| 3,991,745 | 11/1976 | Yoslow et al. | 128/2 |
| 4,007,733 | 2/1977 | Celeste et al. | 128/2 S |
| 4,055,168 | 10/1977 | Miller et al. | 128/2 S |
| 4,392,126 | 7/1983 | Loyola | 340/573 |
| 4,617,525 | 10/1986 | Lloyd | 340/573 |
| 4,665,388 | 5/1987 | Ivie | 340/573 |
| 4,730,625 | 3/1988 | Fraser | 128/781 |
| 4,750,480 | 6/1988 | Jenness | 128/78 |
| 4,871,998 | 10/1989 | Chaillou | 340/573 |
| 4,914,423 | 4/1990 | Fernandez | 340/573 |
| 5,112,176 | 5/1992 | Harris | 340/573 |
| 5,146,929 | 9/1992 | Sawhill | 128/781 |
| 5,168,264 | 12/1992 | Agustin | 340/573 |
| 5,192,254 | 3/1993 | Young | 482/8 |
| 5,304,984 | 4/1994 | Roldan | 340/573 |
| 5,381,801 | 1/1995 | McShane et al. | 128/848 |
| 5,398,697 | 3/1995 | Spielman | 128/781 |

FOREIGN PATENT DOCUMENTS

| | | |
|---|---|---|
| 1196318 | 7/1965 | Germany . |
| WO 89/11247 | 11/1989 | WIPO ........................... A61B 5/10 |
| WO 91/06082 | 5/1991 | WIPO ........................... G08B 21/00 |

Primary Examiner—Michael A. Brown
Attorney, Agent, or Firm—John L. Rogitz

[57] ABSTRACT

A posture training device (100) includes a frame (102) and a module (116) floatingly engaged with the frame (102). The device (100) can be held snugly against the backbone of a person by a belt (122) or garment (124), such that an increase in curvature of the backbone in either the midsagittal plane or a transverse plane moves the module (116) relative to the frame (102). When the module (116) has been moved sufficiently to indicate a poor posture position, a tactile signal generator (160, 162) within the module (116) is activated to vibrate, thereby alerting the person that he or she has assumed a poor posture.

23 Claims, 7 Drawing Sheets

POSTURE TRAINING DEVICE

FIELD OF THE INVENTION

The present invention relates generally to posture training devices, and more particularly to portable, lightweight electro-mechanical devices for generating tactile signals when a user of the device assumes a poor posture.

BACKGROUND

Good posture, generally understood to include the maintenance of the back in a more or less straight conformation, enhances the physical appearance of a person, and reduces the likelihood of injury to the back. Unfortunately, many people develop poor posture early in life, and a person's poor posture may be perpetuated and exacerbated by a sedentary lifestyle. Not only does poor posture detract from a person's physical appearance, poor posture during, e.g., sitting, standing, lifting, etc., can lead to chronic and acute injuries and thus, poor health.

Accordingly, the development of a good posture is highly desirable, for both aesthetic and health reasons. Once a person develops poor posture, however, it is difficult for the person to achieve longterm posture correction, even when the person is motivated to do so. One reason is that a person who has developed poor posture must consciously and continuously attempt to maintain a good posture, at least for an initial correction period that can last weeks and perhaps months. It will readily be appreciated that such a relentless effort can be most difficult to sustain over an extended period.

Fortunately, it has been found that it is possible to help a person sustain a long-term posture correction effort by providing a device that immediately signals to the person that the person's posture is in a less than optimum conformation. One example of such a device is disclosed in U.S. Pat. No. 4,846,157, which discloses an abdomen-circumscribing belt with vibrator, and the vibrator is activated when the person's girth reaches a predetermined girth. In this way, the '157 device, like other devices focussed on abdominal belt systems, can indicate, albeit somewhat indirectly, the poor posture which results from a convexly-curved backbone. Unfortunately, devices such as the '157 device are inherently limited in reliably indicating poor posture because they can only indirectly indicate when the backbone is not being maintained in a more or less straight conformation.

A device which directly measures the curvature of the backbone is disclosed in Patent Cooperation Treaty (PCT) application WO 91/06082, which includes an elongated flexible strap that is positioned along the backbone of a person and held against the person by a belt. Two vibro-tactile emitters are operatively engaged with the strip to generate tactile signals when the strip assumes a predetermined curvature.

While effective for its intended purpose, the invention disclosed in the above-mentioned PCT application is bulky, requiring a rather large buckle for securing the strip to the back. The bulkiness of the device is underscored by the incorporation of two tactile emitters. Presumably, two emitters are required because only a single emitter evidently would not provide sufficient tactile stimulus to the person, given the bulkiness of the device.

Unfortunately, the use of multiple emitters has the inherent drawbacks of increasing the cost, weight, complexity, and battery capacity requirements of the device.

Additionally, the bulkiness of the device disclosed in the above-mentioned PCT application renders it impractical for extended daily use.

Moreover, as recognized by the present invention, it is desirable to indicate poor posture caused not only by curvature of the backbone, but also to indicate poor posture caused by bending of the back transverse to the backbone, as about the waist or as can happen when a person carries his shoulders slouched forward. In either case, the bent back assumes a relatively convex conformation that is associated with poor posture. Because of its nature, however, the above-mention PCT invention is limited to indicating only bending of the back along the backbone, and not transverse to it.

Accordingly, it is an object of the present invention to provide a device for indicating poor back posture. Another object of the present invention is to provide a device for indicating when a person's back is undesirably bent along the backbone and for indicating when the person's back is bent transverse to the backbone. Still another object of the present invention is to provide a posture training device that is relatively compact. Yet another object of the present invention is to provide a posture training device that is easy to use and cost-effective to manufacture.

SUMMARY OF THE INVENTION

A posture training device includes a frame and a vibration module disposed in the center of the frame. The vibration module floats within the frame, and the frame with vibration module can be held against a person's back by a belt or garment to generate a vibro-tactile signal when the person assumes a poor posture. Specifically, the device is held, by forces at its perimeter, against a reference surface of the back, and when the person's backbone is flexed, the mid-sagittal and/or transverse curvature of the back becomes relatively convex. Consequently, the reaction force at the center of the device increases, moving the module within the frame to thereby cause the module to vibrate. Because the device with holder of the present invention provides no support to the body, to stop the vibration, the person must use his or her muscles to move the body back to a good posture. This salubriously conditions and trains the muscles.

Accordingly, a posture training device includes a rigid frame which is positionable against the back of a person at the intersection of a backbone curve defined by the person's backbone and a transverse curve thereof. Also, the device includes a rigid module that is disposed in the frame and that is movably engaged therewith between a good posture position, corresponding to respective first convexities of the curves, and a poor posture position, corresponding to one or both of respective second convexities of the curves. As intended by the present invention, each second convexity is greater than the respective first convexity. A tactile signal generator is mounted on the module for generating a tactile signal when the module is in the poor posture position.

Preferably, a biasing element is disposed between the frame and module to urge the module toward the good posture position. Additionally, the frame includes an electrically insulative contact element. The device further includes an electrical switch which is electrically connected to the tactile signal generator and juxtaposed with the contact element for abutting the contact element when the module is in the poor posture position to thereby activate the tactile signal generator.

In a presently preferred embodiment, the electrical switch includes a stationary contact mounted on the module.

Moreover, the switch includes a cantilever contact mounted on the module and biased toward an open configuration, wherein the contacts are distanced from each other, the contact element urging the cantilever contact to a closed configuration when the module is in the poor posture position, wherein the contacts contact each other to activate the tactile signal generator. An adjustment element is engaged with the switch and manipulable to establish the poor posture position of the module.

As intended herein, the tactile signal generator includes a direct current (DC) battery and a DC motor electrically connected to the battery. Preferably, the DC motor includes a rotor and a mass which is eccentrically coupled to the rotor to cause the motor to vibrate when the motor is energized by the battery.

In a particularly preferred embodiment, the module is formed with opposed wedge-shaped detents, each defining a flat face. Furthermore, the frame is formed with opposed ramped surfaces, each terminating in respective flat surfaces. With this structural combination, the module can be engaged with the frame by advancing the module into the opening with the detents riding on the ramped surfaces until the detents clear the ramped surfaces and abut the respective flat surfaces.

In another aspect of the present invention, a device is disclosed which is engageable with a person's back. The person's back defines a backbone dimension and a transverse dimension orthogonal to the backbone dimension. As intended by the present invention, the device includes a holder that is engageable with the person's back. Also, a frame is engaged with the holder such that the frame is positioned against the back when the holder is engaged with the back. A vibration module is floatingly engaged with the frame for movement relative to the frame between a good posture position, wherein the module does not vibrate, and a poor posture position, wherein the module vibrates, the good posture position corresponding to a first configuration of the back in the backbone dimension, the poor posture position corresponding to a second configuration of the back in the backbone dimension, the second configuration being generally more convex than the first configuration.

In still another aspect, a vibrator device includes a rigid frame defining an opening. A rigid vibration module is movably engaged with the frame for movement relative to the frame between a first position, wherein the module does not vibrate, and a second position, wherein the module vibrates. Additionally, an edge holding member urges at least two opposed edges of the frame toward a surface to thereby urge the vibration module against the surface. Consequently, movement of the surface causes movement of the vibration module between the first and second positions.

The details of the present invention, both as to its structure and operation, can best be understood in reference to the accompanying drawings, in which like reference numerals refer to like parts, and in which:

BRIEF DESCRIPTION OF THE DRAWINGS

Referring initially to FIG. 1, a person's spine is labelled in accordance with accepted nomenclature of the art. FIG. 1A shows a person whose spine exhibits good posture, i.e., an acceptable curvature. In contrast, FIG. 1AA shows a person whose spine exhibits poor posture, i.e., an excessive curvature.

Figure 1:
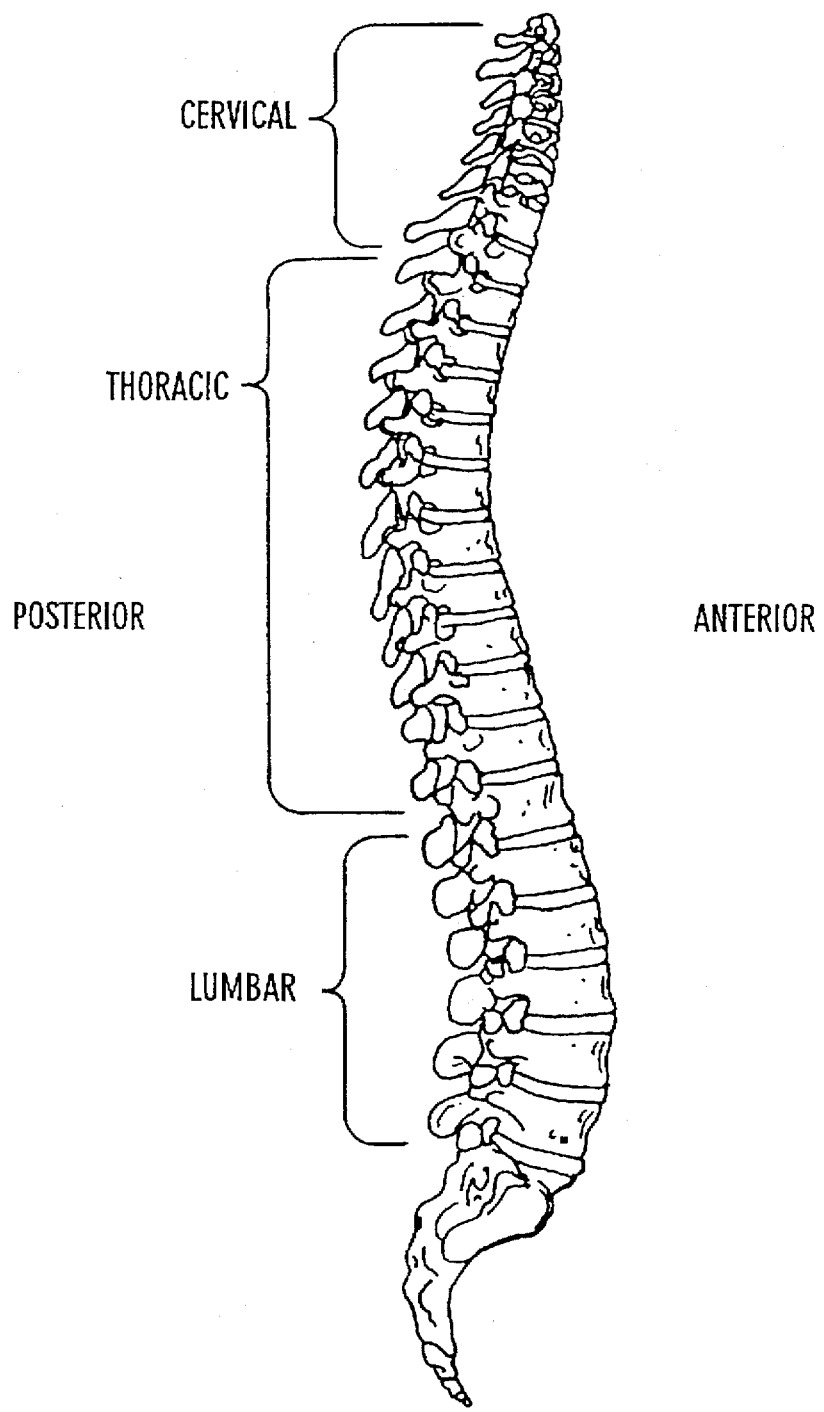
FIG. 1 is a lateral view of a normal adult spine in the standing position, showing the lumbar, thoracic, and cervical regions and their normal curvatures.
Figure 1A:
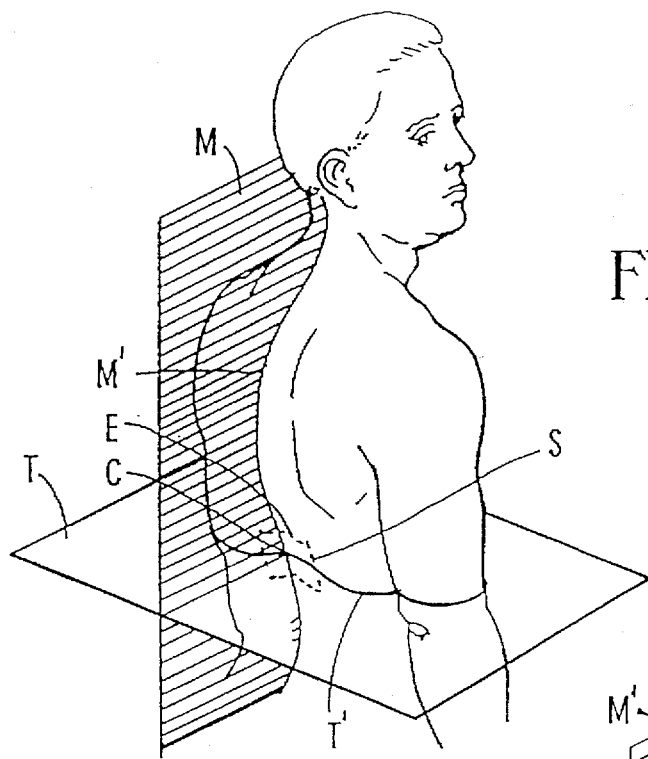
FIG. 1A is a perspective view of a person exhibiting good posture.
Figure 1E:
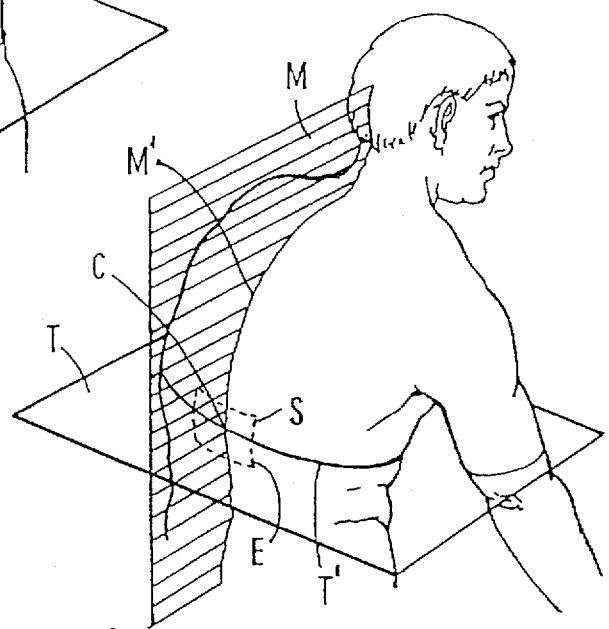
FIG. 1E is a perspective view of a person exhibiting poor posture.

As intended by the present invention, a measurement of curvature may be defined as $k=1/r$, wherein k is curvature, and r is the radius of the particular segment of the spine being measured. For the purposes of this specification positive curvature (positive value of k) will be taken to mean a convex curvature to the posterior surface of the body such as in the thoracic region, while a negative curvature (negative value of k) concave to the posterior surface of the body is shown in the lumbar region. For example, the curvature of the lumbar region of the spine shown in FIG. 1A is approximately $-0.1$ inches$^{-1}$. My research shows that a device with an alarm setting adjustable over a range for values of k between 0 and 0.8 inches$^{-1}$ will accommodate the lumbar, thoracic, and cervical spines of most individuals.

In accordance with the present invention, the device of the present invention is intended to be positioned against a reference surface "S", shown in FIGS. 1A and 1AA. As shown, the reference surface "S" has a center "C" which is defined by the intersection of two curves M' and T'. The first curve M' is defined by the intersection of a midsagittal plane "M" and the body, while the second curve T' is defined by the intersection of the body with a transverse plane "T" that is orthogonal to the midsagittal plane "M". As further shown, the midsagittal plane "M" passes through the spine of the person.

As recognized herein and as can be appreciated in reference to FIGS. 1A and 1AA, flexion of the spine changes the contour of the reference surface "S". More particularly, flexion of the spine causes the reference surface "S" to assume a convex contour in both the midsagittal and transverse planes "M'", "T'", as shown in FIG. 1AA, relative to its contour when the person assumes a good posture, shown in FIG. 1A. Consequently, the center "C" of the reference surface "S" is disposed posteriorly relative to edges "E" of the reference surface "S", under poor posture conditions.

As further recognized herein, an object can be held by its perimeter against the reference surface "S", with reaction forces being produced between the object and reference surface "S" when the reference surface "S" changes contour. Per principles discussed below, these reaction forces can be sensed and a posture signal generated in response thereto, to alert the person that he/she has assumed a poor posture.

Figure 1B:
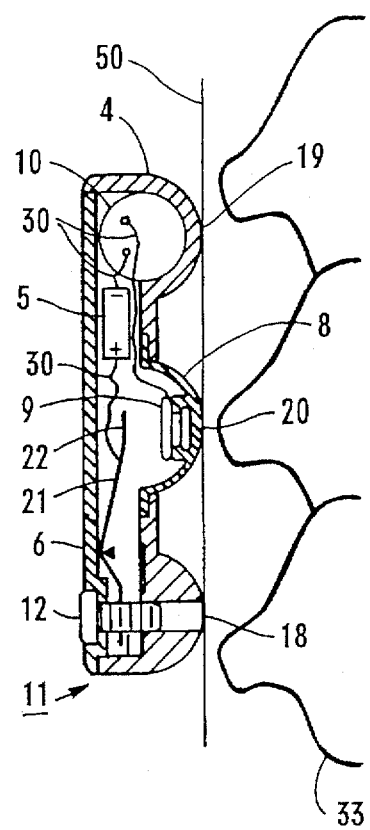
FIG. 1B is a cross-sectional view of one embodiment of the present invention, showing the device in the good posture configuration.
Figure 1C:
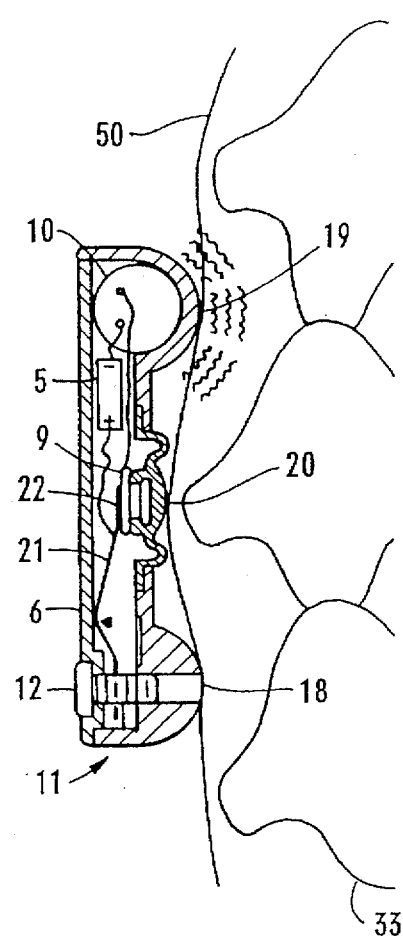
FIG. 1C is a cross-sectional view of the embodiment shown in FIG. 1B, showing the device in the poor posture configuration.

Now referring to FIG. 1B, a curvature alarm device 11 is held firmly against the surface of a person's back 50 at the spinal column 33. The section of spine in FIG. 1B is shown arbitrarily straight and may be located anywhere along the spinal column. The device comprises a battery 5, a first contact 22 which is an extension of adjustable arm 21, a second contact 9 mounted on flexible elastomeric diaphragm 8, and adjusting screw 12 for adjusting adjustable arm 21. As shown in FIGS. 1B and 1C, the housing 4 has a geometry which includes two lobes which contact the back at positions 18 and 19. The fixed points 18 and 19 remain biased against the back of the wearer by the tension of a belt (not shown). Diaphragm 8 has a convex geometry with the high point at point 20 midway between points 18 and 19. Contact 9 is attached to diaphragm 8 and is free to move as pressure is exerted against point 20 by an increase in spinal curvature between points 18 and 19. When the curvature increases to the point where the adjusted gap shown in FIG. 1B is closed as shown in FIG. 1C, the circuit comprised of battery 5, contacts 22 and 9, and the buzzer 10, is closed and the buzzer alerts the wearer of his incorrect posture. If the wearer corrects his or her posture the contacts separate due to the resiliency of diaphragm 8 and the circuit is opened. A lid 6 covers the housing 4.

Figure 1D:
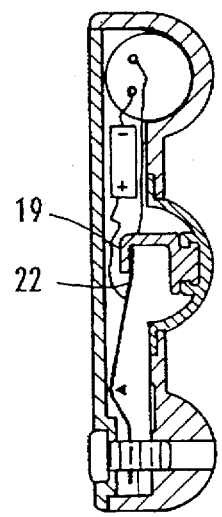
FIG. 1D shows an alternative contact arrangement which causes an alarm condition at either extreme of the excursion of the indicator.

The contact arrangement shown in FIGS. 1B and 1C is the arrangement of the preferred embodiment and causes an alarm condition when curvature increases. An alternative contact arrangement is shown in FIG. 1D wherein the position of contact 22 is adjusted to float within a gap in contact 9 when the diaphragm is partially depressed. The contacts will then close if curvature either increases or decreases. Numerous other contact arrangements and methods of adjustment are easily imagined.

Figure 2:
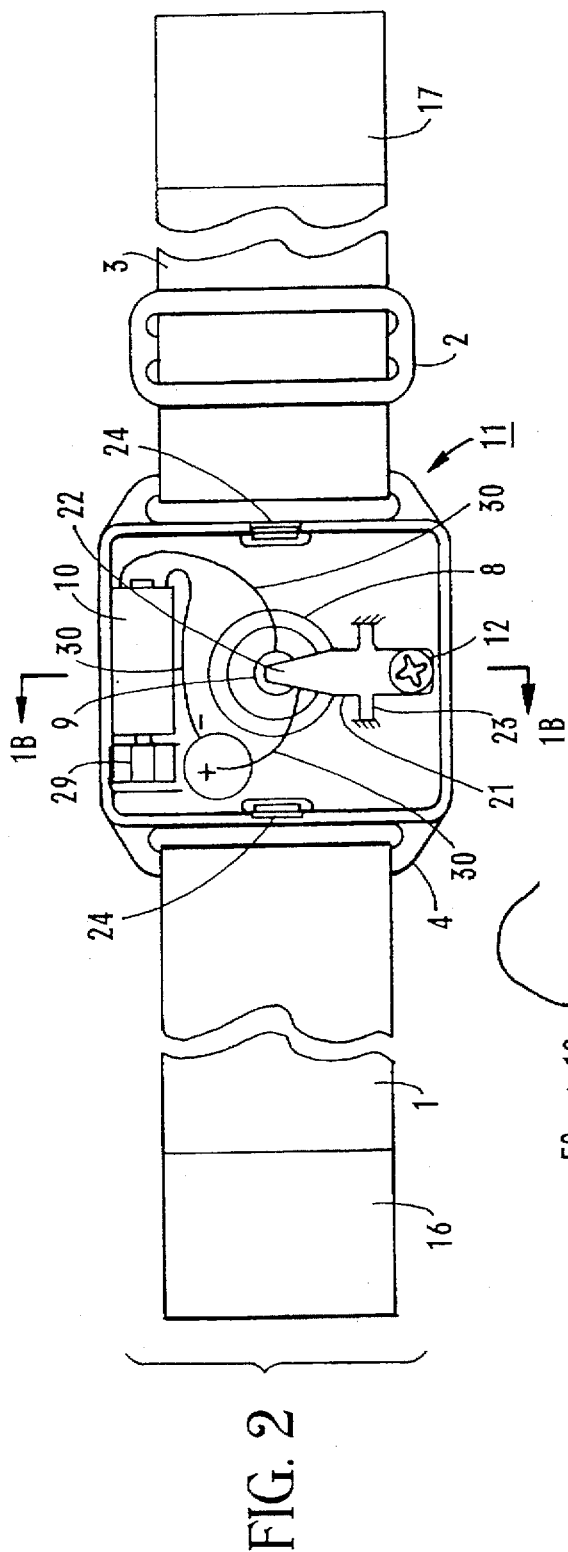
FIG. 2 is a plan view of the embodiment shown in FIG. 1B, with the cover shown as being transparent.

FIG. 2 shows a top view of the device shown if FIG. 1B where the lid 6 is assumed to be transparent for illustrative purposes. Torsion arms 23, integral to arm 21, are anchored to the lid 6. Rotation of adjusting screw 12, with the screw head against a surface on the lid 6 (FIG. 1B), and threaded shank engaged with arm 21, causes arm 21 to rotate about the torsion arms 23. This changes the gap between contact 9 and contact 22 which determines the amount of spinal curvature required before the buzzer 10 is activated. An elastic belt comprised of sections 1 and 3 supports the device against the body. One end of belt section 3 is passed through slider 2, looped through housing 4, and anchored to slider 2, which provides a length adjustment means for the belt. Attached to the ends of belt sections 2 and 3 are male and female hook and loop fastener sections 16 and 17 respectively for joining the ends of belt sections 2 and 3.

Referring still to FIGS. 1B and 2, snap features 24 on the lid 6 engage with detentes in the housing 4 to hold the lid in place. A battery 5, preferably a 1.5V alkaline battery, is shown in generalized format in the figures. Insulated wires 30, or formed metal conductors (not shown) connect the battery 5 to contact 22 and buzzer 10, and contact 9 to buzzer 10.

The buzzer 10 is preferably a pager motor, of the type commonly found in pagers, consisting of a coreless DC motor with an eccentric mass 29 mounted to the motor shaft. The buzzer 10 is rigidly or semi-rigidly mounted to housing 4. When the buzzer 10 is activated by excessive spinal curvature, the spinning, eccentric mass 29 causes vibration which is transmitted through the housing 4 to the surface of the back 50. The vibration is easily detected due to the proximity to the spinal column, but is not easily noticed by others.

Figure 3:
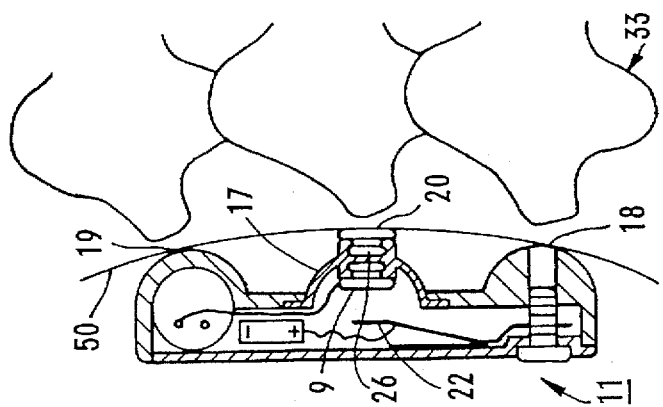
FIG. 3 is a sectional view through the midsagittal plane showing how the device detects the curvature of the spine.
Figure 5:
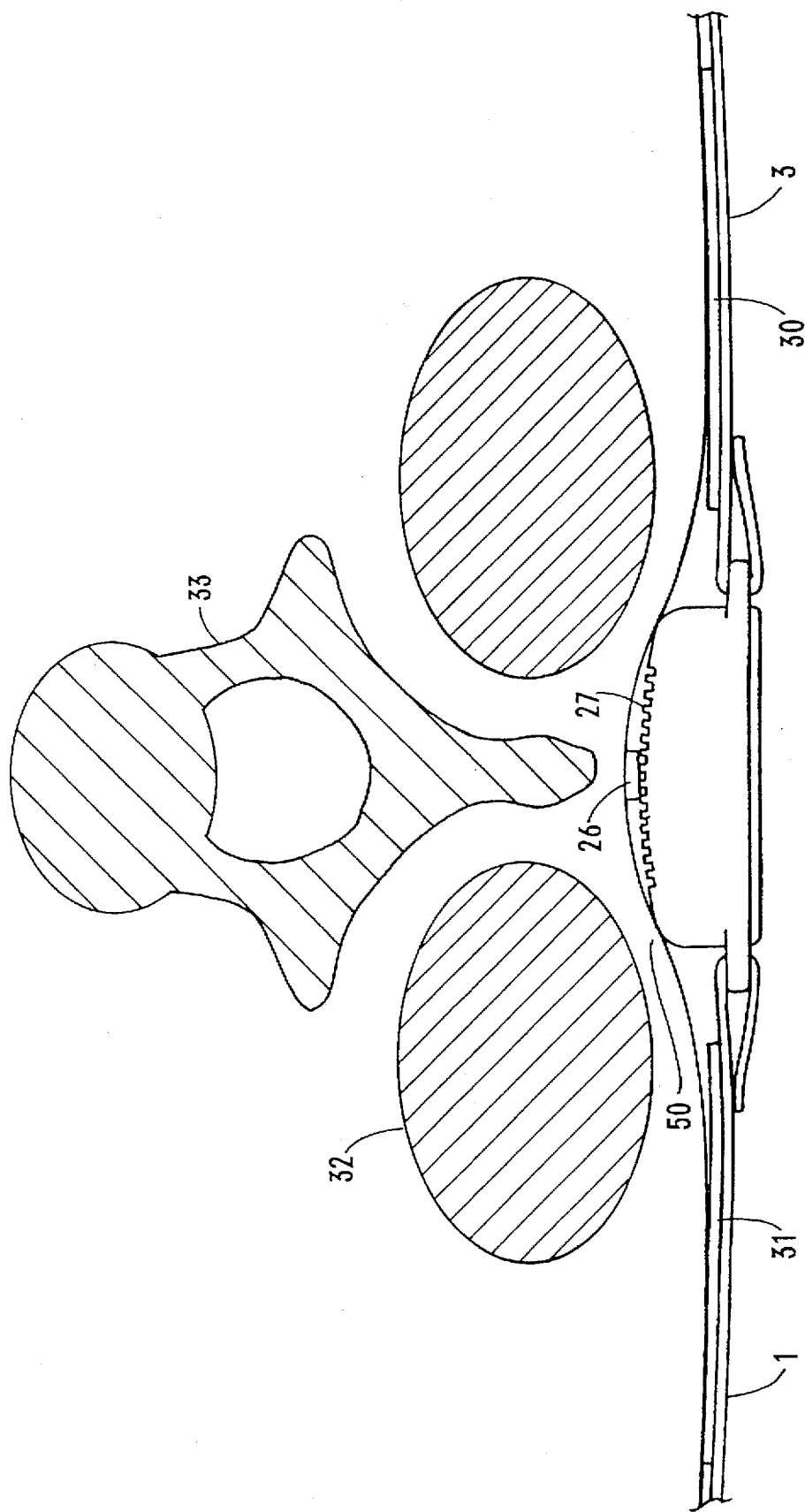
FIG. 5 is a view in a transverse plane of the body showing an end view of the embodiment shown in FIG. 4, in juxtaposition with a person's vertebrae and erector spinae muscles.

FIGS. 3 and 5 show the device of FIGS. 1B and 1C with a button 26 snapped into modified diaphragm 17. The button 26 provides intimate contact with the surface of the back 50 in the event that the midsagittal curve M' or transverse curve T' (FIGS. 1A, and 1B) are negative or convex. The button 26, and the gap between contacts 22 and 9 combine to determine the amount of allowable curvature before the device alarms.

Figure 4:
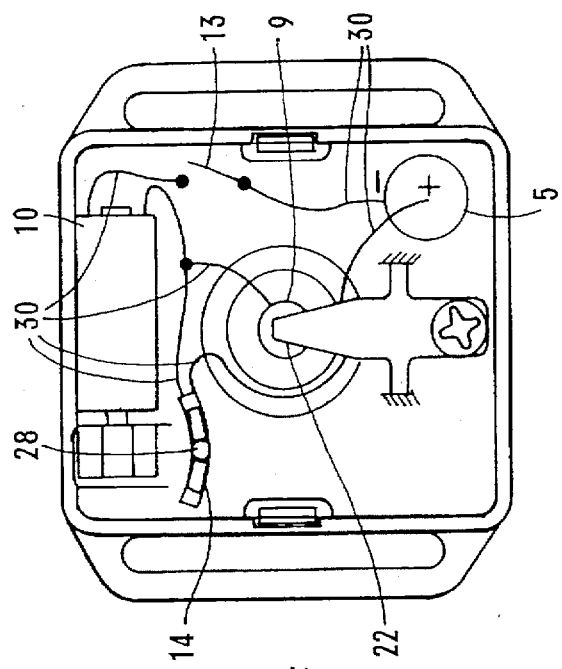
FIG. 4 is a plan view of an alternate embodiment of the present invention, with the belt removed and the cover shown transparent.

FIG. 4 shows the device of the preceding figures modified by the addition of a curved mercury switch 14, and a conventional SPST switch 13, such as Radio Shack model 275-406, so that sideways bending, or curvature of the spine viewed posteriorly, may be detected. The purpose of SPST switch 13 is to prevent accidental activation of the buzzer 10 when the device is not in use. Switch 13 is also useful if the wearer wishes to deactivate the device while performing activities which might cause nuisance alarms. The two contacts internal to switch 14 are insulated except at either end. As the wearer leans to one side or the other, the mercury blob 28 will flow down hill, eventually coming the either extreme of the switch, and closing the contacts. The circuit elements are contact 22, contact 9, mercury switch 14, SPST switch 13, battery 5, and buzzer 10. The elements are arranged in the manner shown in FIG. 4 such that either sideways bending, which closes the internal contacts of the mercury switch 14, or forward bending which closes contacts 22 and 9, will activate the buzzer 10.

FIG. 5 shows an end view of the device of FIGS. 1B and 1C as well as a sectional view of the back in a transverse plane. The cleft, or negative curvature, between the erector spinae muscles 32 with low point over the spine 33, is typical of many people's physique. Button 26 provides intimate contact with the surface 50 of the back. This view clearly shows how an increase in the convexity of the surface 50 of the back, in the transverse plane, can produce pressure against button 26 and activate the device independent of the curvature in the midsagittal plane. The curved, serrated ridge 27 is shaped to an average person's transverse curve, and the serrations provide increased friction with the surface of the back 50 when they contact surface 50. Pads of high friction material 31 are attached to belt sections 1 and 3 to further increase friction against surface 50, and discourage migration of the device.

All of the embodiments shown provide adjustment for the range of curvature within which there will be no alarm and outside of which the alarm is activated. This avoids the problem of over-constraining the posture of the wearer and causing fatigue. Typical ranges of allowable (no alarm condition) curvature for the lumbar spine of a seated adult are given in TABLE 1. Two embodiments are shown, one which alarms only during forward bending (positive curvature) of the spine, and one which alarms during both forward and backward bending of the spine. Ranges are given for both the lumbar and thoracic regions. If the wearer is performing activities which require a full range of motion such as lifting of objects, the range of allowable curvature may need to be increased to avoid too frequent alarm conditions. The device should be adjusted while being worn at the intended location on the wearer's back and as the wearer performs the activities in which his posture needs improvement. The designs of all of the embodiments shown allow for adjustment beyond the typical ranges shown in TABLE 1.

TABLE 1

| Typical Acceptable Curvature Ranges, k (in$^{-1}$) | | |
|---|---|---|
| BENDING DIRECTION | LUMBAR | THORACIC |
| FORWARD ONLY | k < 0.1 | k < 0.1 |
| FORWARD AND BACKWARD | −0.17 < k < 0.1 | 0 < k < 0.1 |

Now referring to FIGS. 6–11, a posture training device, generally designated 100, includes a rigid, preferably injection-molded plastic, frame 102 that is positionable against the back of a person at the intersection of a midsagittal curve "M'" (FIG. 1A), which generally describes the contour of the backbone of the person, and a transverse curve "T'" that is orthogonal to the midsagittal curve "M'". Specifically, the device 100 is positionable against the reference surface "S" shown in FIG. 1A.

Figure 6:
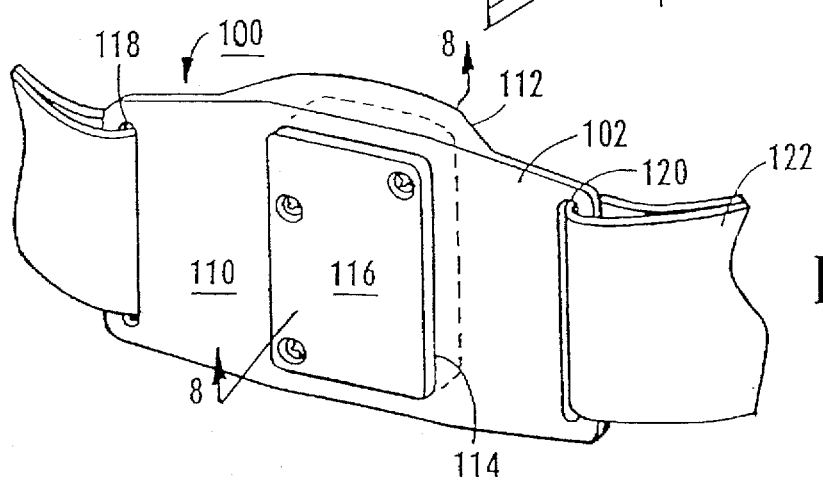
FIG. 6 is a perspective view of an alternate embodiment of the present invention, shown held snugly against the back of a person.

As shown in FIG. 6, the frame 102 is unitarily formed with a flat, generally parallelepiped-shaped exposed surface 110 and a curved, partially-cylindrical contact surface 112. As further shown, the contact surface 112 is opposed to the exposed surface 110, with the contact surface 112 facing the back of the person when the device 100 is positioned against the back as intended.

When the device 100 is snugly held as intended against the back, the area of the back over which the device 100 is positioned is a reference area, the center of which is defined by the intersection of the midsagittal curve "M'" and the transverse curve "T'". Consequently, flexion of the person's spine, which tend to cause the midsagittal curve "M'" and/or transverse curve "T'" to become relatively more convex than they otherwise would be, will cause a concomitant posterior movement of the center of the reference area relative to the edges of the reference area. As disclosed in greater detail below, this movement is sensed by the device 100, and when the magnitude of the movement is sufficiently great, the device 100 generates a tactile signal that is sensed by the person as an indication of poor posture.

FIG. 6 further shows that the frame 102 is hollow, in that the frame 102 defines a central, generally parallelepiped-shaped opening 114. A rigid hollow injection-molded plastic vibration module 116 is positioned in the opening 114 and is movably engaged with the frame 102. Preferably, the module 116 is floatingly engaged with the frame 102 within the opening 114.

As intended by the present invention, "floatingly engaged" means that the module 116 moves relative to the frame 102 when either the midsagittal curve "M'" or transverse curve "T'" assumes a relatively convex configuration. In other words, when the surface of the back against which the module 116 is positioned changes geometry, reaction forces are produced at the intersection of the midsagittal curve "M'" and transverse curve "T'", and because the perimeter of the frame 102 is held securely on the back, the reaction forces move the module 116 relative to the frame 102.

More particularly, the module 116 can move relative to the frame 102 toward a good posture position, corresponding to respective first convexities of the curves "M'", "T'". It is to be understood that this good posture position corresponds to the good posture configuration of the back in the midsagittal dimension and in the transverse dimension shown in FIG. 1A.

Furthermore, the module 116 can move relative to the frame 102 toward a poor posture position, corresponding to one or both of respective second convexities of the curves "M'", "T'". It is to be understood that this poor posture position corresponds to the poor posture configuration of the back in one or both of the midsagittal and transverse dimensions, with the second configuration being generally more convex than the first configuration, as shown in FIG. 1AA.

As disclosed in detail below, a tactile signal generator is mounted on the vibration module 116 for generating a tactile signal when the vibration module 116 is in the poor posture position. In other words, in the good posture position the module 116 does not vibrate, whereas the tactile signal generator causes the module 116 to vibrate when it is in the poor posture position.

In one presently preferred embodiment, the frame 102 is formed with opposed left and right edge slots 118, 120, and a holder, e.g., a belt 122, can be engaged with the slots 118, 120 to hold the device 100 snugly against the back of the person. Together, the belt 122 and edge slots 118, 120 establish an edge holding member. Alternatively, referring briefly to FIG. 10, the holder of the present invention can be a snug elastic garment 124 which has a back side 126. The back side 126 includes one or more receptacles, e.g., pockets 128, that are oriented along the centerline of the back side 126 (and, hence, that are positioned over the backbone of the person when the garment 124 is worn by the person). The device 100 can be disposed in one of the pockets 128 to hold the device 100 against the intersection of the midsagittal curve and transverse curve by essentially urging the edges of the frame 102 toward the person. It is to be understood that the garment 124 can be a vest, halter top, bra, or other athletic garment as appropriate. Together, a pocket 128 of the garment 124, in cooperation with the opposed edges of the frame 102, establish an edge holding member.

Figure 7:
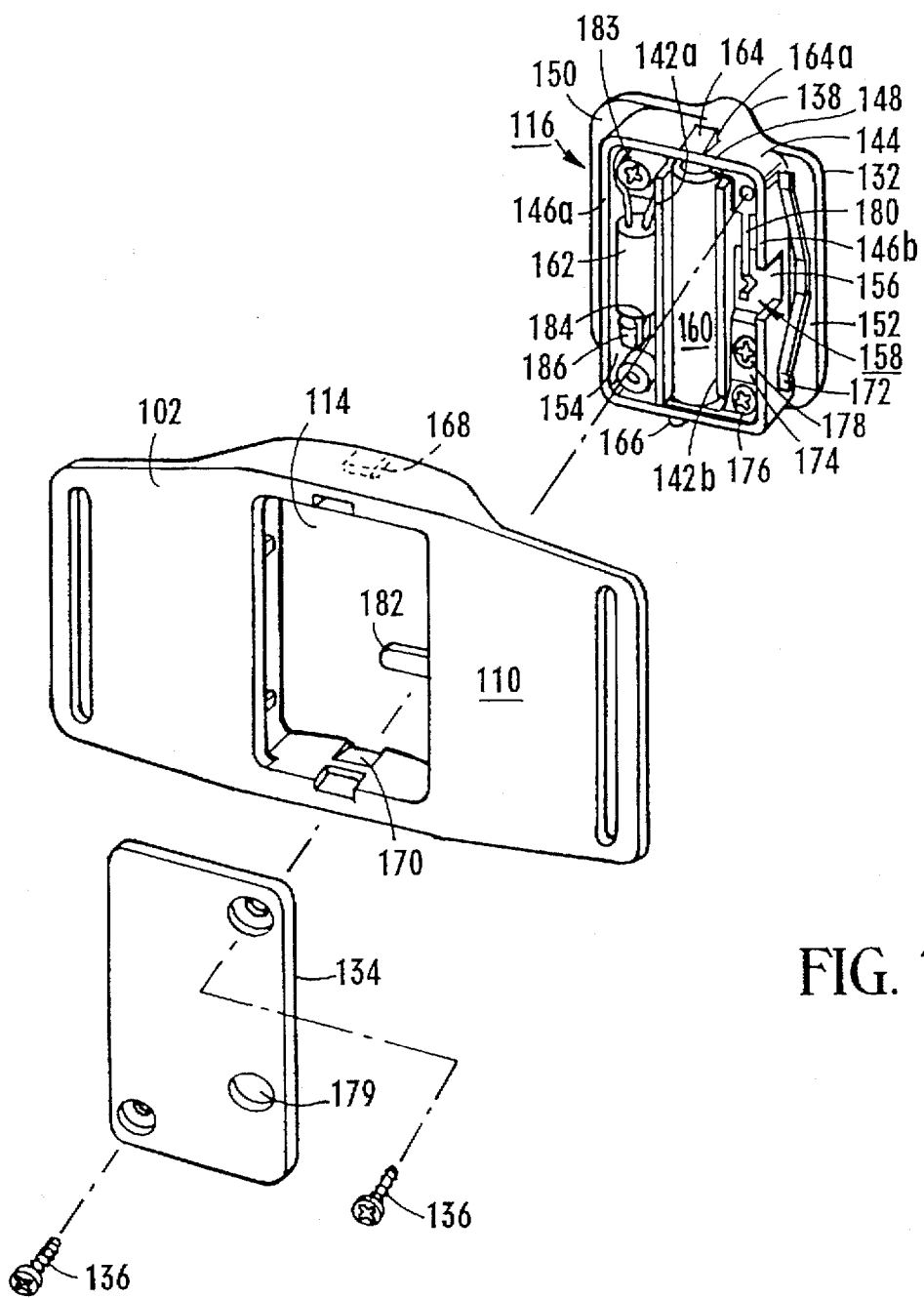
FIG. 7 is an exploded view of the device shown in FIG. 6.
Figure 8:
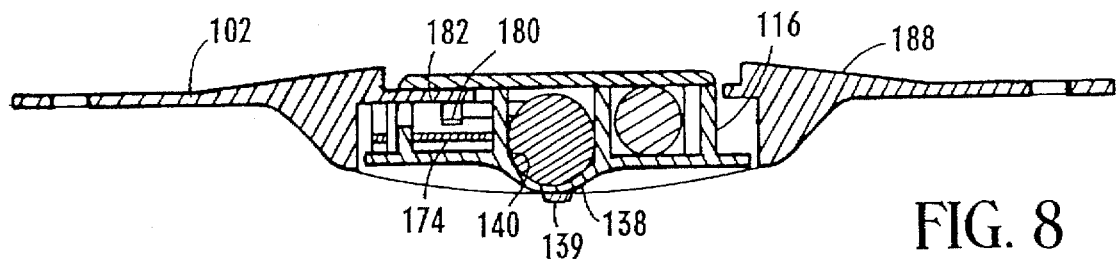
FIG. 8 is a cross-sectional view, as seen along the line 8—8 in FIG. 6, with the module in the good posture position.

In cross-reference to FIGS. 6–8, the details of the module 116 can be seen. As shown best in FIG. 7, the module 116 includes a tactile signal generator housing 132 and a flat, parallelepiped-shaped back plate 134 which is held against the housing 132 by two fastener screws 136. As shown best in FIG. 6, the back plate 134 is somewhat flush with the exposed surface 110 of the frame 102 when the module 116 is engaged with the frame 102.

FIGS. 7 and 8 best show that the housing 132 is formed with a convex, partially cylindrical, elongate contact surface 138 which establishes an opposed concave battery trough 140. If desired, soft pads 139 may be adhered to the surface 138 to better match the particular transverse curve "T'" of the person. It is to be understood that when the device 100 is worn as intended, the contact surface 138 is positioned against the backbone of the person with the long dimension of the contact surface 138 being parallel to the backbone. Preferably, the longitudinal centerline of the contact surface 138 is more or less flush with and contiguous to the centerline of the contact surface 112 of the frame 102. As recognized by the present invention, the above-disclosed conformation of the contact surfaces 112, 138 maximizes the area of the back 104 contacted by the device 100 when the back is in the neutral configuration, i.e., when the person exhibits good posture.

As shown in FIG. 7, the battery trough 140 is centrally formed in the housing 132 and is bounded along its long sides by first and second interior walls 142a, 142b. The housing 132 further includes a rectangular perimeter wall 144 which includes opposed first and second long perimeter segments 146a, 146b and opposed short perimeter segments 148. Additionally, left and right flanges 150, 152 are formed on the contact surface 138 of the housing 132, and the flanges 150, 152 extend laterally outwardly from the perimeter wall 144.

With the combination of structure shown, a vibration motor cavity 154 is established between the first interior wall 142a and first long perimeter segment 146a. Also, a switch cavity 156 is established between the second interior wall 142b and second long perimeter segment 146b. As more fully disclosed below, and electrical switch, generally designated 158, is disposed in the switch cavity 156. In contrast, a preferably type AAA direct current (DC) battery 160 is disposed in the battery trough 140, and a DC motor 162 is disposed in the vibration motor cavity 154. Together, the battery 160 and motor 162 establish a tactile signal generator.

FIG. 7 best shows that the opposed short perimeter segments 148 are formed with respective wedge-shaped detents 164, 166 which are identically configured with each other. As shown, taking the detent 164 as an example, the detent 164 defines a flat face 164a. As further shown, the frame 102 is formed with opposed ramped surfaces 168, 170, each terminating in a respective flat surface. As a consequence of this combination of structure, the module 116 can be engaged with the frame 102 by advancing the module 116 into the opening 114, with the detents 164, 166 riding on the ramped surfaces 168, 170 until the detents 164, 166 clear the ramped surfaces 168, 170. When the detents 164, 166 clear the ramped surfaces 168, 170, the flat faces of the detents 164, 166 abut the respective flat surfaces of the frame 102 to hold the module 116 in floating engagement with the frame 102.

FIG. 7 also shows that a biasing element, preferably a metal leaf spring 172, is attached to one of the flanges 150, 152 of the housing 132. As shown, the leaf spring 172 is disposed between the frame 102 and module 116 to urge the module 116 toward the good posture position. If desired, a second leaf spring (not shown) can be attached to the other flange 152, 150. The spring constant of the spring 172 is established to optimize the amplitude of vibration of the spring-mass system established by device 100.

FIGS. 7 and 8 show that the switch 158 includes a stationary spring metal contact 174 that is disposed in the switch cavity 156. It is to be understood that the stationary contact 174 is electrically connected to the positive terminal of the battery 160. As shown, the stationary contact 174 is held in the switch cavity 156 by a holding screw 176 and an adjustment screw 178, with the adjustment screw 178 being accessible through an opening 179 in the back plate 134. In accordance with the present invention, the stationary contact 174 is materially biased to urge against the adjustment screw 178.

Also, the switch 158 includes a leaf spring cantilever contact 180 that is mounted on the module 116 by one of the fastener screws 136. It is to be understood that the cantilever contact 180 is electrically connected to the motor 162, with the motor 162 being electrically connected to the negative terminal of the battery 160 via a negative contact 183.

In accordance with the present invention, the cantilever contact 180 is biased toward an open configuration shown in FIG. 8, wherein the contacts 174, 180 are distanced from each other. Additionally, the cantilever contact 180 can be urged to a closed configuration, shown in FIG. 9, wherein the contacts 174, 180 electrically contact each other.

FIGS. 7 and 8 show that the frame 102 includes an electrically insulative contact element 182 that extends into the opening 114, such that it is juxtaposed with the cantilever contact 180 and sandwiched between the back plate 134 and housing 132. Thus, the module 116 is retained in the opening 114 by the cooperation of structure between the contact element 182, opening 114, and perimeter wall 144.

Figure 9:
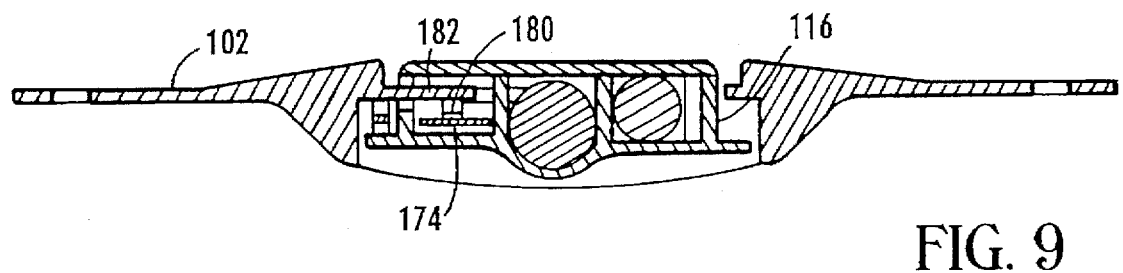
FIG. 9 is a cross-sectional view, as would be seen along the line 8—8 in FIG. 6, with the module in the poor posture position.
Figure 10:
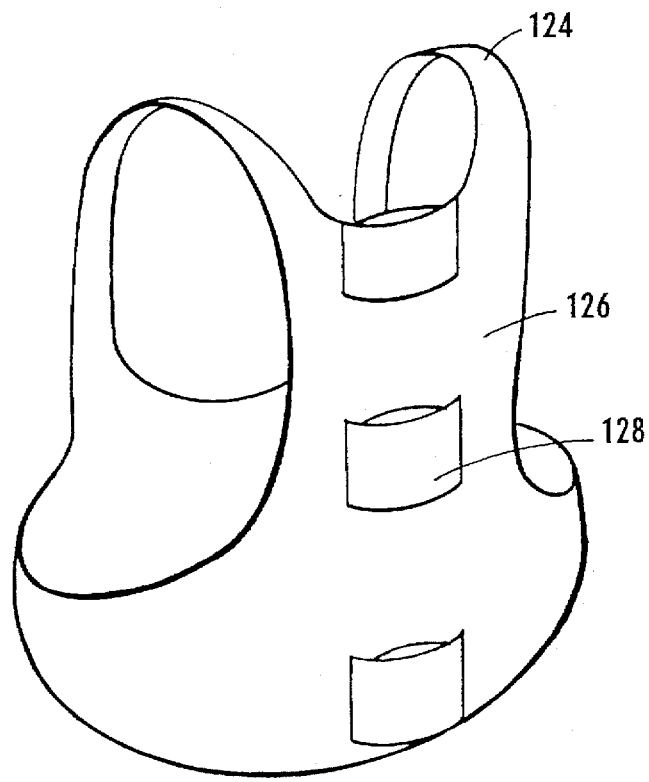
FIG. 10 is a perspective view of a garment for holding the posture training device of the present invention snugly against the back of a person.

Moreover, it may now be appreciated that when the module 116 is in the poor posture position shown in FIG. 9, the contact element 182 abuts the cantilever contact 180. In turn, the cantilever contact 180 is urged against the stationary contact 174 to complete the electrical circuit between the battery 160 and motor 162. On the other hand, when the module 116 is in a position other than the poor posture position, e.g., the good posture position shown in FIG. 8, the contact element 182 does not urge against the cantilever contact 180 with sufficient force to cause the cantilever element 180 to contact the stationary contact 174. It may now be further appreciated that the adjustment screw 178 can be manipulated to adjust the distance between the contacts 174, 180 and, hence, to establish the poor posture position of the module 116.

Preferably, the motor 162 is an unbalanced motor of the type found in telephone pagers. Accordingly, the motor 162 includes a rotor 184 and an asymmetric mass 186 which is eccentrically coupled to the rotor 184. The motor 162 (and, hence, device 100) is consequently caused to vibrate when the motor 162 is energized by the battery 160.

FIG. 8 shows that, if desired, the exposed surface of the frame 102 can be formed with raised ramps 188. The ramps 188 prevent the belt 122 from contacting the back plate 134 of the module 116 and thus potentially interfering with the movement of the module 116.

The operation of the device 100 may now be understood. The device 100 is held against the reference surface "S" of the back of a person by a belt or garment as described, with the contact surface 138 of the module 116 generally parallel to and positioned over the backbone. It is to be understood that as intended herein, the contact surface 138 is held against the backbone when the contact surface directly contacts the skin, as well as when a garment is interposed between the skin and contact surface 138.

When the person exhibits relatively good posture, the reference surface "S" of the back is not unduly convex. Consequently, the force of the spring 172 against the frame 102 urges the contact element 182 away from the cantilever contact 180 of the module 116, thereby maintaining an open electrical circuit between the battery 160 and motor 162.

On the other hand, when the person assumes a posture which is sufficiently poor such that the back overcomes the bias of the spring 172 and urges against the module 116, the module 116 moves relative to the frame 102 toward the poor posture position. When the module 116 is in the poor posture position shown in FIG. 9, the electrical circuit between the battery 160 and motor 162 is completed, thereby causing the device 100 to vibrate.

More specifically, when the person assumes a poor posture, the back 104 moves the module 116 relative to the frame 102 such that the contact element 182 urges the cantilever contact 180 against the stationary contact 174, thereby activating the vibration motor 162. The degree of "poorness" of the posture required to move the module 116 to the poor posture position and thereby activate the vibration motor 162 is established by the position of the adjustment screw 178. If desired, the device 100 can, instead of or in addition to generating a tactile signal when the module 116 is in the poor position, generate an audible alarm, or electrical stimulus, or even cause data to be transmitted to a data recording device.

While the particular POSTURE TRAINING DEVICE as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims.

What is claimed is:

1. A posture training device, comprising:
    a rigid frame positionable against the back of a person at the intersection of a backbone curve defined by the person's backbone and a transverse curve thereof;
    a rigid generally box-shaped hollow module disposed in the frame and movably engaged therewith between a good posture position, corresponding to respective first convexities of the curves, and a poor posture position, corresponding to one or both of respective second convexities of the curves, each second convexity being greater than the respective first convexity; and
    a tactile signal generator mounted on the module for generating a tactile signal when the module is in the poor posture position.

2. The device of claim 1, further comprising a biasing element disposed between the frame and module to urge the module toward the good posture position.

3. The device of claim 2, wherein the frame includes an electrically insulative contact element, and the device further comprises an electrical switch electrically connected to the tactile signal generator and juxtaposed with the contact element for abutting the contact element when the module is in the poor posture position to thereby activate the tactile signal generator.

4. The device of claim 3, wherein the electrical switch includes a stationary contact mounted on the module and a cantilever contact mounted on the module and biased toward an open configuration, wherein the contacts are distanced from each other, the contact element urging the cantilever contact to a closed configuration when the module is in the poor posture position, wherein the contacts contact each other to activate the tactile signal generator.

5. The device of claim 4, wherein the tactile signal generator includes a direct current (DC) battery and a DC motor electrically connected to the battery, the DC motor including a rotor and a mass eccentrically coupled to the rotor to cause the motor to vibrate when the motor is energized by the battery.

6. The device of claim 5, wherein the frame defines a central opening, and the contact element extends into opening.

7. The device of claim 6, further comprising an adjustment element engaged with the switch and manipulable to establish the poor posture position of the module.

8. The device of claim 7, wherein the module is formed with opposed wedge-shaped detents, each defining a flat face, and the frame is formed with opposed ramped surfaces, each terminating in respective flat surfaces, such that the module can be engaged with the frame by advancing the module into the opening with the detents riding on the ramped surfaces until the detents clear the ramped surfaces and abut the respective flat surfaces.

9. The device of claim 8, in combination with a garment including at least one receptacle for holding the frame with module therein.

10. A device engageable with a person's back defining a backbone dimension and a transverse dimension orthogonal to the backbone dimension, the device comprising:
    a holder engageable with the person's back;
    a frame engaged with the holder such that the frame is positioned against the back when the holder is engaged with the back; and
    a hollow generally box-shaped vibration module floatingly engaged with the frame for movement relative to the frame between a good posture position, wherein the module does not vibrate, and a poor posture position, wherein the module vibrates, the good posture position corresponding to a first configuration of the back in the backbone dimension, the poor posture position corresponding to a second configuration of the back in the backbone dimension, the second configuration being generally more convex than the first configuration.

11. The device of claim 10, wherein the module is engaged with the frame such that good posture position also corresponds to a first configuration of the back in the transverse dimension and such that the poor posture position corresponds to a second configuration of the back in the transverse dimension, the second configuration being generally more convex than the first configuration.

12. The device of claim 11, further comprising a biasing element disposed between the frame and module to urge the module toward the good posture position.

13. The device of claim 11, further comprising:
    a tactile signal generator mounted on the module for generating a tactile signal and thereby causing the module to vibrate when the module is in the poor posture position.

14. The device of claim 13, wherein the frame includes an electrically insulative contact element, and the device further comprises an electrical switch electrically connected to the tactile signal generator and juxtaposed with the contact element for abutting the contact element when the module is in the poor posture position to thereby activate the tactile signal generator.

15. The device of claim 14, wherein the electrical switch includes a stationary contact mounted on the module and a cantilever contact mounted on the module and biased toward an open configuration, wherein the contacts are distanced from each other, the contact element urging the cantilever contact to a closed configuration when the module is in the poor posture position, wherein the contacts contact each other to activate the tactile signal generator.

16. The device of claim 14, wherein the frame and module are made of rigid plastic, the frame defines a central opening, and the contact element extends into opening.

17. The device of claim 14, further comprising an adjustment element engaged with the switch and manipulable to establish the poor posture position of the module.

18. The device of claim 13, wherein the tactile signal generator includes a direct current (DC) battery and a DC motor electrically connected to the battery, the DC motor including a rotor and a mass eccentrically coupled to the rotor to cause the motor to vibrate when the motor is energized by the battery.

19. The device of claim 11, wherein the module is formed with a central convex contact surface for abutting the back of the person along the backbone dimension thereof.

20. The device of claim 11, wherein the holder is selected from the group of holders consisting of: a garment including at least one receptacle for holding the frame with module therein; and a belt.

21. The device of claim 11, wherein the holder is a garment including at least one receptacle for holding the frame with module therein.

22. The device of claim 11, wherein the module is formed with opposed wedge-shaped detents, each defining a flat face, and the frame is formed with opposed ramped surfaces, each terminating in respective flat surfaces, such that the module can be engaged with the frame by advancing the module into the opening with the detents riding on the ramped surfaces until the detents clear the ramped surfaces and abut the respective flat surfaces.

23. A vibrator device, comprising:

a rigid frame defining an opening;

a rigid hollow generally box-shaped vibration module movably engaged with the frame for movement relative to the frame between a first position, wherein the module does not vibrate, and a second position, wherein the module vibrates; and an edge holding member for urging at least two opposed edges of the frame toward a surface to thereby urge the vibration module against the surface, such that movement of the surface causes movement of the vibration module between the first and second positions.

* * * * *